(12) United States Patent
Yeatman et al.

(10) Patent No.: US 7,815,722 B2
(45) Date of Patent: Oct. 19, 2010

(54) PLANAR MICROMACHINED VALVE AND THERMAL DESORBER

(75) Inventors: Eric Yeatman, London (GB); Richard Syms, London (GB)

(73) Assignee: Microsaic Systems, Ltd., Surrey (GB)

( * ) Notice: Subject to any disclaimer, the term of this patent is extended or adjusted under 35 U.S.C. 154(b) by 932 days.

(21) Appl. No.: 11/700,395

(22) Filed: Jan. 31, 2007

(65) Prior Publication Data

US 2007/0186776 A1 Aug. 16, 2007

(30) Foreign Application Priority Data

Jan. 31, 2006 (GB) ................................. 0601902.0

(51) Int. Cl.
*B01D 53/02* (2006.01)

(52) U.S. Cl. .................... 96/143; 73/863.12; 73/863.73; 251/129.01; 422/88

(58) Field of Classification Search .............. 73/863.12, 73/863.73; 96/143; 251/129.01; 422/88

See application file for complete search history.

(56) References Cited

U.S. PATENT DOCUMENTS 3,057,376 A * 10/1962 Agutter et al. .............. 137/594

(Continued)

FOREIGN PATENT DOCUMENTS

WO   WO 2004/065830   5/2004

OTHER PUBLICATIONS

Webster's Third New International Dictionary, Unabridged, 1993.*

(Continued)

*Primary Examiner*—Jason M Greene
*Assistant Examiner*—Anthony Shumate
(74) *Attorney, Agent, or Firm*—Bishop & Diehl, Ltd.

(57) ABSTRACT

This invention provides a pre-concentrator device including an electrostatically operated valve and an electrically heated desorber, the electrostatically operated valve comprising a movable flap or membrane carrying a chemically adsorbing coating, suspended by an elastic element above an orifice in an insulated substrate. The device is constructed by planer processing. The flap or membrane can be deflected towards the substrate to block the flow of gas through the orifice by applying a voltage between the substrate and the membrane. The coating provides an adsorbing surface for a volatile organic compound. The coating may be heated electrically, by applying an alternating voltage between the substrate and the flap, thermally desorbing any adsorbed chemical species. When combined with other similar valves in a stacked assembly, the device may be used in a chemical pre-concentrator with very low dead volume.

15 Claims, 6 Drawing Sheets

U.S. PATENT DOCUMENTS

| | | | | |
|---|---|---|---|---|
| 3,306,111 | A * | 2/1967 | Ferrin | 73/863.73 |
| 3,386,472 | A * | 6/1968 | Szonntagh | 137/597 |
| 4,805,441 | A * | 2/1989 | Sides et al. | 73/23.25 |
| 5,142,143 | A * | 8/1992 | Fite et al. | 250/288 |
| 5,345,809 | A * | 9/1994 | Corrigan et al. | 73/23.2 |
| 5,481,110 | A | 1/1996 | Krishnaswamy et al. | |
| 5,671,905 | A * | 9/1997 | Hopkins, Jr. | 251/129.01 |
| 5,719,324 | A * | 2/1998 | Thundat et al. | 73/24.01 |
| 5,822,170 | A | 10/1998 | Cabuz et al. | |
| 5,882,496 | A | 3/1999 | Northrup et al. | |
| 6,112,602 | A | 9/2000 | Mitra | |
| 6,126,140 | A * | 10/2000 | Johnson et al. | 251/129.01 |
| 6,171,378 | B1 | 1/2001 | Manginell et al. | |
| 6,527,835 | B1 * | 3/2003 | Manginell et al. | 96/102 |
| 6,590,267 | B1 * | 7/2003 | Goodwin-Johansson et al. | 257/415 |
| 6,598,461 | B2 * | 7/2003 | Hering et al. | 73/23.41 |
| 6,604,406 | B1 * | 8/2003 | Linker et al. | 73/28.02 |
| 6,914,220 | B2 | 7/2005 | Tian et al. | |
| 7,141,786 | B2 * | 11/2006 | McGann et al. | 250/287 |
| 2005/0001182 | A1 | 1/2005 | Wise et al. | |
| 2005/0095722 | A1 | 5/2005 | McGill et al. | |

OTHER PUBLICATIONS

Feng, Chaohua et al., *Two-Stage Microtrap as an Injection Device for Continuous On-Line Gas Chromatographic Monitoring, Journal of Chromatography A*, 805 (1998) 169-176.

Mitra, Somenath et al., *Continuous Gas Chromatographic Monitoring of Low Concentration Sample Streams Using an On-Line Microtrap, Journal of Chromatography*, 648 (1993) 415-421.

Tian, Wei-Cheng, *Microfabricated Preconcentrator-Focuser for a Microscale Gas Chromatograph, Journal of Microelectromechanical Systems*, vol. 12, No. 3, Jun. 2003.

* cited by examiner a)

b)

c)

a)

b)

a)

b)

a)

b)

PLANAR MICROMACHINED VALVE AND THERMAL DESORBER

CROSS-REFERENCE TO RELATED APPLICATIONS

This application claims priority to United Kingdom Patent Application No. GB0601902.0, filed Jan. 31, 2006, which is expressly incorporated herein by reference and made a part hereof.

FEDERALLY SPONSORED RESEARCH OR DEVELOPMENT

Not applicable.

TECHNICAL FIELD

The invention relates to valves and in particular to planar micromachined valves having a thermal desorber incorporated therein. The invention more particularly relates to a pre-concentrator device incorporating such a valve.

BACKGROUND OF THE INVENTION

Portable chemical analysis systems are required for the detection of explosives and other hazardous material. Such systems may be based on separation by gas chromatography followed by detection, or on ion mobility spectrometry, or on mass spectrometry. Because the analyte concentration is vanishingly low, other devices are often incorporated to improve the detectable limit. One such device is a chemical pre-concentrator, a device for enhancing the concentration of a volatile organic compound (VOC) in a gas stream prior to analysis.

The main components of a pre-concentrator system are shown in FIG. 1. The pre-concentrator element itself is a trap that will preferentially adsorb a dilute VOC from a gas stream. Adsorption is often based on the use of a porous material or a chemically reactive layer of material. Examples of the former are carbon granules and sol-gel glasses, and examples of the latter are functionalized polymers. This material 101 is held on a mechanical support 102, which can be heated. Usually heating is carried out electrically.

The trap is placed in a small enclosure 103 between three valves. The first valve 104 connects to the gas flow input 105, and the second valve 106 connects to the gas flow output 107. The third valve 108 connects to the subsequent analysis system 109. Pre-concentration involves a repetition of adsorption and desorption steps.

FIG. 2 shows the adsorption step. The input and output gas flow valves 201 and 202 are opened, and the valve 203 connecting to the analysis system is closed. A gas stream 204 containing a small fraction of VOC 205 together with a large fraction of other molecules 206 is allowed to pass over or through the trap. Most of the VOC 207 is adsorbed on the trapping layer 208, while the remainder of the gas stream emerges as exhaust 209.

FIG. 3 shows the desorption step. The input and output gas flow valves 301 and 302 are closed, and the connecting valve 303 is opened. The adsorbed molecules are desorbed, usually by rapidly raising the temperature of the chemically sensitive layer 304 using the heater 305, and a concentrated flux of the VOC 306 is passed into the analysis system 307.

Macroscopic pre-concentrators are available commercially. Pre-concentrator performance is defined in terms of the efficiency (i.e., the fraction of the desired analyte that is retained) and of the concentration factor (i.e. the increase in the desired analyte concentration). To maximize the efficiency, the surface area of the trap should be large as possible, and the sensitized coating highly attractive to the desired analyte, while to maximize the concentration factor, dead volumes should be as small as possible.

To reduce cycle times, the heated element should have low thermal mass. However, to increase the concentration factor even further without increasing the time needed for desorption, pre-concentrators are often used in a cascade consisting of a first trap with a large volume followed by a second trap with a small volume. The first trap has high efficiency but a long desorption time while the second trap has a short desorption time. Pre-concentrators containing even more stages are constructed in an analogous way.

The above considerations suggest that pre-concentrators are ideal candidates for miniaturization, and small traps based on capillaries were developed in the 1990s [Mitra and Yun 1993; Feng and Mitra 1998; U.S. Pat. No. 6,112,602]. Increased integration with other components such as valves and gas chromatographs can be achieved by planar processing, and several planar pre-concentrators with thin-film heaters have been developed [U.S. Pat. No. 5,481,110; U.S. Pat. No. 6,171,378]. Micromachined heaters with deep, etched trays filled with sorbent granules have also been demonstrated [Tian et al. 2003; U.S. Pat. No. 6,914,220]. A flow-though pre-concentrator based on a sorbent polymer coating on a perforated heater has also been developed [US 20050095722]. None of these configurations is entirely suitable for a compact system, since the valves needed for overall operation are often added by hybrid integration, causing an increase in dead volume and a reduction in concentration factor.

Accordingly there is a need for an improved pre-concentrator.

SUMMARY OF THE INVENTION

These and other problems are addressed by the present invention in providing a valve for a thermal desorber in a pre-concentration device by combining the two elements directly in a compact, stackable assembly with low dead volume that can be formed by low cost planar processing.

A first embodiment of the invention provides a pre-concentrator device configured to provide for a detection of one or more species present in a gas flow, the device including a trap through which the gas may flow, entry of gas into the trap through an orifice being controlled by a moveable membrane which is moveable between a first position wherein the gas is free to move through the orifice and into the trap and a second position wherein the membrane seals the orifice preventing the flow of gas into the trap, and wherein the membrane is provided with an adsorption coating configured to selectively adsorb the species present in the gas during the flow of gas through the trap, and wherein on sealing of the orifice the membrane is heatable so as to effect a desorption of the previously adsorbed species from the adsorption coating.

By incorporating an adsorption surface onto the membrane that seals the trap it is possible to provide dual functionality on the membrane. Such dual functionality reduces the number of parts that are required for the pre-concentrator device and also eases the control functionality required for operation of the device.

Within the context of the invention it will be appreciated that the adsorption coating could be provided as a layer or coating on the membrane or indeed could be provided as a second integer that is integrally formed with the membrane or indeed sequentially added to the membrane.

The moveable membrane is typically electrostatically operable and may be provided as a moveable flap suspended by an elastic element.

The trap is desirably formed as a sealable area with an inner wall of the area being formed from a substrate provided of an insulating material. The orifice is desirably provided through the insulating substrate, a closure of the membrane effecting a contact between a portion of the membrane and the insulating substrate.

By applying a voltage between the insulating surface and the membrane it is possible to effect a movement of the membrane.

The device is desirably configured to provide for a sensing of a chemical species, although it will be appreciated that a suitably defined adsorption surface could provide for a sensing of biological materials also or instead of the chemical species.

Where the species is a chemical species, it is typically a volatile organic chemical.

The substrate may be formed in a semiconductor material through a patterning process. The adsorption coating may be provided in a mount and the flap, the elastic element and the mount may be formed in the semiconductor. Other configurations or applications may provide for the formation in a metal. Where provided in a semiconductor, the insulator may be provided by the oxide layer of a semiconductor.

The adsorbing coating may be provided in typical embodiments by a porous material or a functionalized polymer. It will be appreciated that the exact nature of the coating will be defined by the species which is desired to be detected using the device.

The trap may include a second sealable orifice through which the gas may exit the trap. Such an orifice may be sealable by a valve, the valve configured to seal the trap on movement of the membrane to the second position.

The invention also provides a pre-concentrator system comprising:

at least one pre-concentrator device, the trap defining an enclosure, the enclosure including at least three valves through which gaseous flow through the trap may be controlled. One of the three valves may be provided by the membrane with integrally formed adsorption coating, in which case two additional valves may be required.

An opening of two of the valves provides for a flow of gas across the adsorption coating, and a closure of two of the valves and the opening of a third valve enables a transfer of material desorbed from the heated coating to a concentrated analyte stream for subsequent analysis.

The invention also provides in accordance with a further embodiment a device including a combined electrostatically operated valve and an electrically heated desorber, comprising:

a movable flap carrying a chemically selective coating which is suspended by an elastic element above an orifice in an insulated substrate.

These and other features and benefit will be understood with reference to the following exemplary embodiments

DETAILED DESCRIPTION

Figure 1:
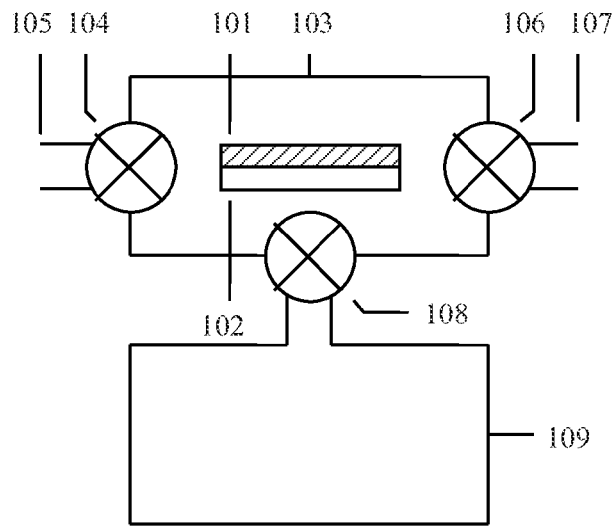
FIG. 1 shows the elements of a chemical preconcentrator, as described in prior art.
Figure 2:
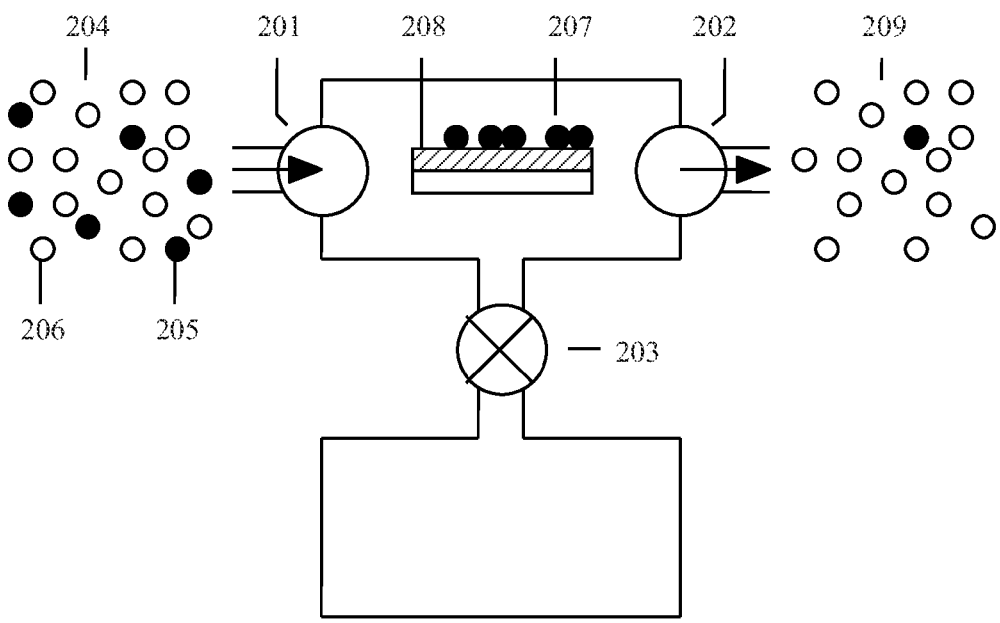
FIG. 2 shows the adsorption step of chemical preconcentration, as described in prior art.
Figure 3:
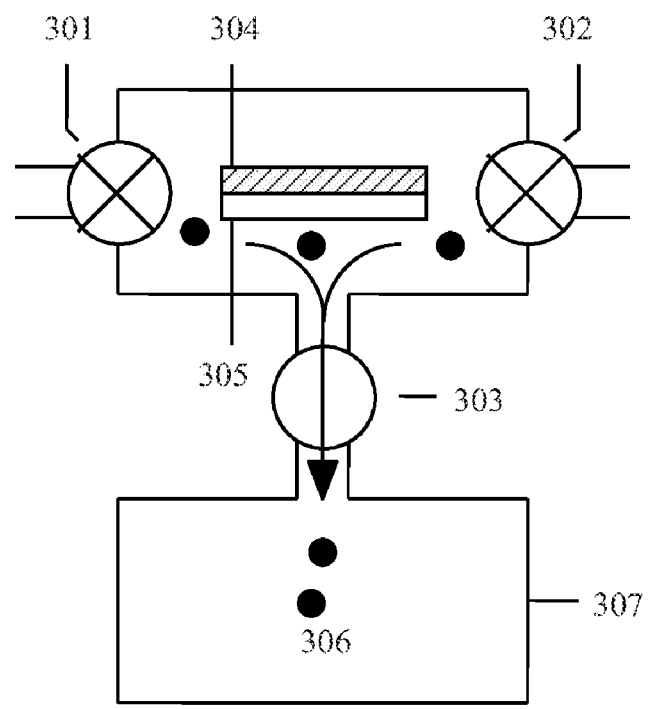
FIG. 3 shows the desorption step of chemical preconcentration, as described in prior art.

A detailed description of preferred exemplary embodiments of the invention is provided with reference to FIGS. 4-8.

FIG. 4a shows a section view of the device, and FIGS. 4b and 4c show plan views of the upper and lower surfaces of the device. The device is formed using a three-layer stack, consisting of a substrate 401, a device layer 402 and a separating layer 403. The substrate 401 and the device layer 402 are formed from conducting or semiconducting materials, while the separating layer 403 is an insulator. The substrate layer contains one or more orifices 404, which also passes through the insulating layer. The device layer 402 contains a thin, movable flap or membrane 405 attached to the insulating layer at at least one fixed point 406 and separated from the insulating layer by a small clearance 407 otherwise. A gas stream 420 containing a small fraction of species 430 together with a large fraction of other molecules 440 is allowed to pass over the one or more orifices 404.

Surrounding the flap or movable membrane 405 is a continuous perimeter of raised material 408, separated from the flap or movable membrane 405 by a clearance 410 except at the fixed point 406. This perimeter can form a gas-tight seal to a further planar surface to which the device is attached.

The flap or movable membrane 405 is subdivided into sections consisting of flexible elastic members 411a, 411b, a rigid valve closure plate 412, and a mechanical support 413 for an adsorbing coating 414 constituting a chemically selective coating. The movable membrane 405 comprises a moveable flap. The mechanical support 413 is suspended over the one or more orifices 404 by the elastic members 411a and 411b. The mechanical support 413 constitutes a desorber mount on which the adsorbing coating 414 is mounted and from which the one or more species 430 is desorbed. The adsorbing coating 414 constitutes a trap configured to selectively adsorb one or more species present in the gas during the flow of gas through the trap. Exposed surfaces 415, 415b and suitable layers are provided to allow single-sided electrical contact to the substrate and the device layer, respectively, via bond wires.

The layout shown is illustrative and not exclusive. For example, the elastic members may be cantilevers, beams or membranes, or any combination thereof that will allow motion of the valve closure flap towards the orifice, and more than one support point may be provided. If a continuous membrane is used, an opening may be provided in the membrane to allow the passage of gas. Similarly, the support for the adsorbing coating may be flat, perforated or textured to provide a suitable surface area.

The substrate and device layers may be formed in a semiconductor such as silicon, and the insulating layer may be formed in silicon dioxide. In this case, a suitable starting material is a bonded silicon-on-insulator wafer, which consists of a second silicon wafer bonded to a first, oxidized silicon wafer, and polished back to the desired thickness.

If a bonded silicon-on-insulator wafer is used, the structure shown may be fabricated using methods well known in the art. The silicon features may be formed using methods including but not restricted to photolithography followed by deep reactive ion etching. The silicon dioxide features may again be formed using methods including but not restricted to isotropic wet chemical etching followed by thermal oxidation. However, other combinations of metals, semiconductors and insulators that provide the required function and that may be structured by planar processing would be suitable.

It will also be appreciated that the substrate and device layers may alternatively be formed separately and then bonded together, for example if the nature of the chemically selective coating is incompatible with some processing steps.

Similarly, the adsorbing coating may consist of any material that provides a suitably sensitive layer, for example a sol-gel glass or a functionalized polymer. A variety of methods well known in the art may be used to deposit both types of material, including but not restricted to spin coating and laser deposition. Similarly, a variety of methods may be used to pattern both types of material, including but not restricted to photolithography followed by plasma etching. Some materials may such as polymers may also be deposited and patterned simultaneously by localized, matrix-assisted laser transfer.

Figure 5:
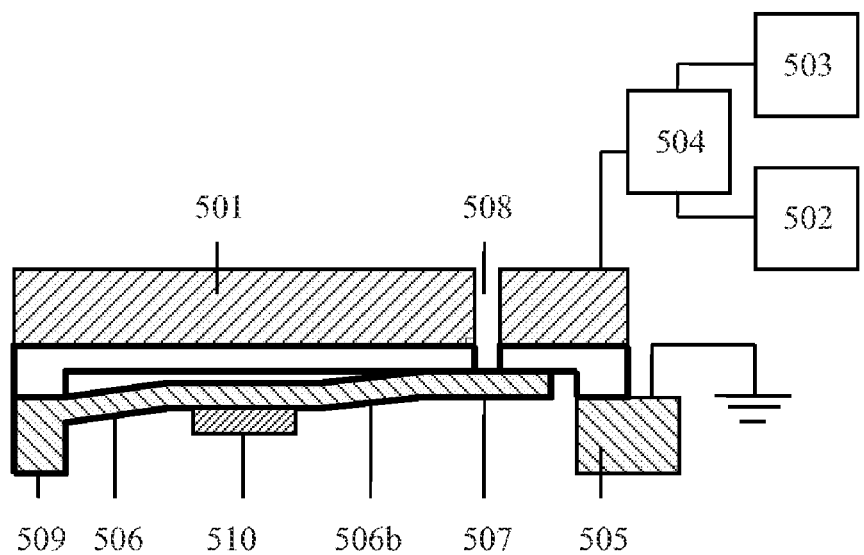
FIG. 5 shows a section view of the operation of the device, according to the present invention.

Operation of the device is shown in FIG. 5. Here the substrate 501 is connected to a source of direct current (DC) voltage 502 and a source of radiofrequency (RF) alternating voltage 503 by a suitable combining device 504. Both voltage sources may be controlled remotely, for example by a microprocessor. The device layer 505 is grounded. However, the arrangement shown is not intended to be exclusive, and any arrangement that allows a provision of separate DC and RF voltages between the substrate and flap would be suitable.

Application of the DC voltage will generate an electrostatic force between the movable flap and the substrate, which will cause the flap to be attracted towards the substrate, bending the flexible elements 506, 506b. If the voltage is sufficient, the valve closure plate 507 will contact the insulating layer at the orifice 508, closing the orifice. This action can prevent the flow of gas through the orifice, providing the operation of a gas valve.

At this point, no current will flow between the valve closure plate and the substrate because of the presence of the insulating layer, which blocks DC current. However, once the valve is closed, additional application of the RF voltage can cause an alternating current to flow between the valve closure plate and the substrate, because the two are capacitatively coupled together by the insulating layer. Part of this current will flow through the flap from the anchor point 509 to the valve closure plate 507, passing through the mechanical support carrying the chemically sensitive layer 510 and causing its temperature to rise by resistive heating. If the temperature rise is sufficient, desorbtion of any adsorbed molecules will occur. Thus, the two actions of flow control and desorption may be combined in a single element, using separate DC and RF voltages.

Other parts of the current will flow elsewhere, for example between the substrate 501 and the perimeter 505. This current may be minimized using a thicker insulating layer in these regions. The resistance of the desirably heated elements may be controlled by careful selection of dimensions, and of the electrical properties of the material used. If the material is a semiconductor such as silicon, these properties may be controlled using a suitable dopant. The suspension may be folded or otherwise meandered to prevent a closed valve being opened by thermal expansion of the suspension during the desorption step.

It will be apparent to those skilled in the art that the operation of closing the valve and heating the desorber may also be carried out using RF voltages alone, since an RF voltage will also provide an electrostatic force between the movable flap and the substrate.

Figure 4:
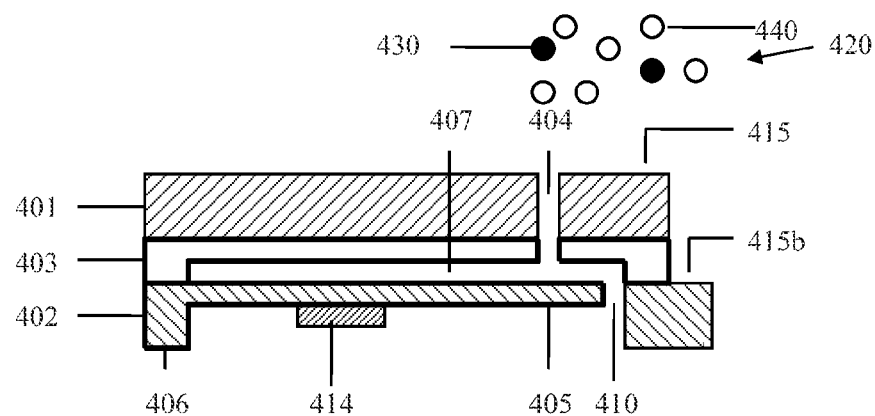
FIG. 4a shows a section view of the device.
FIGS. 4b and 4c show plan views of the substrate and device layers, according to the present invention.
Figure 4:
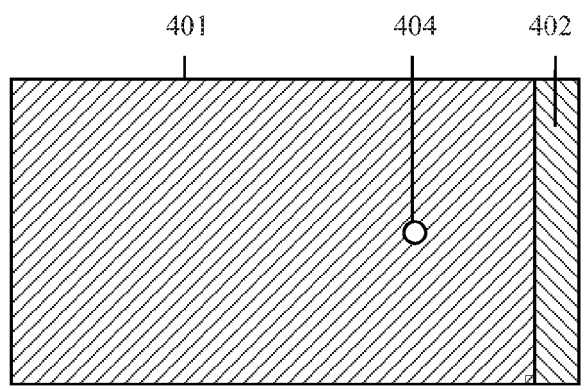
Figure 4:
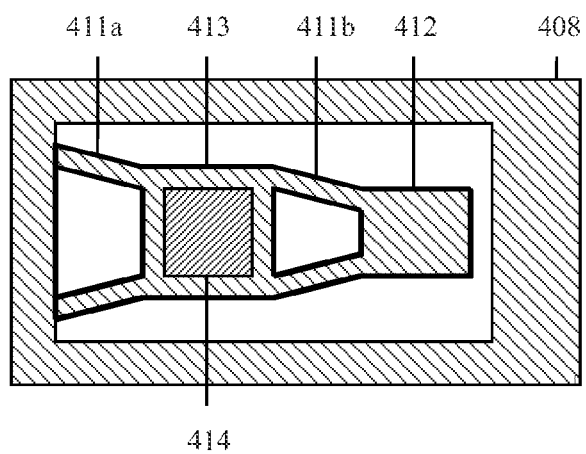

It will also be apparent to those skilled in the art that several structures of the type shown in FIG. 4 may be combined in a single substrate, using the methods of planar processing. For example, FIG. 6a shows in section and FIG. 6b shows in plan an assembly of two valves 601 and 602. In this figure and the subsequent figures the electrical contact points are not shown, it being assumed that they may be provided using the stepped arrangement shown in FIG. 4.

Figure 6:
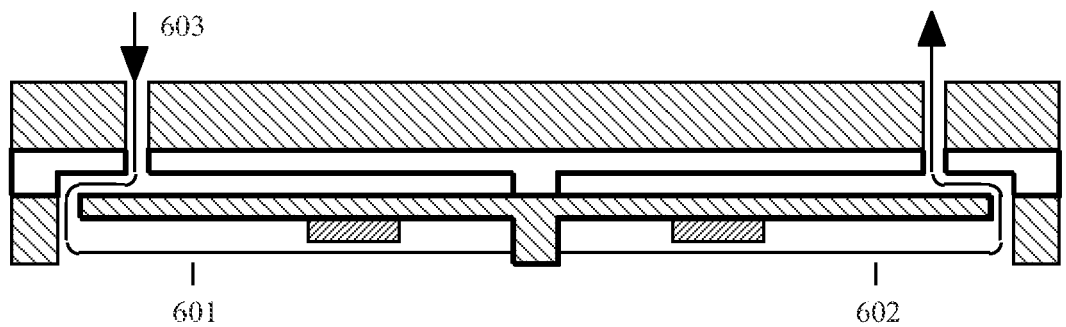
FIG. 6a shows a section view of two devices combined in a single substrate and FIG. 6b shows a plan view of the device layer, according to the present invention.
Figure 6:
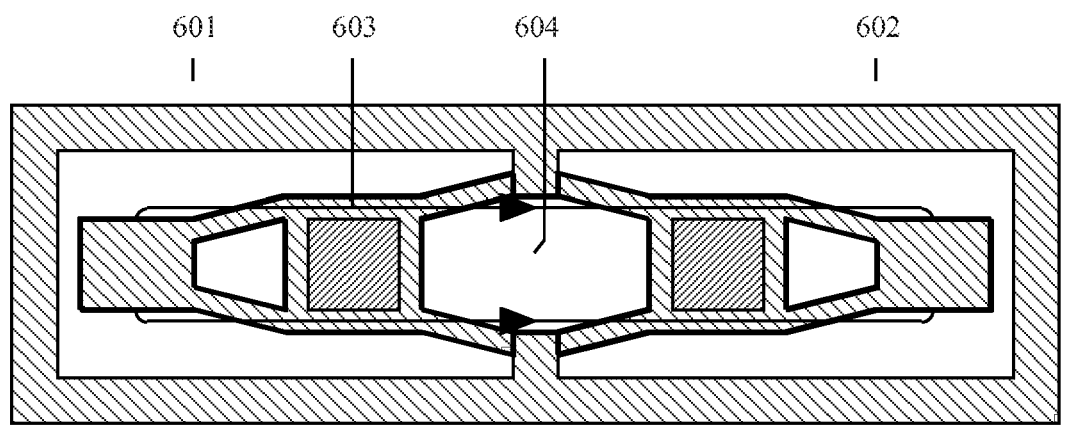

The two valves in FIG. 6 are arranged back to back. When the two valves are opened, a gas stream 603 may flow in through the orifice in the first valve 601 and out through the orifice in the second valve 602, a channel 604 being etched in the device layer between the two valves to allow passage of gas therebetween. In this case the gas stream will pass over the chemically sensitive layers on the two valves.

Similarly, FIG. 7a shows in section and FIG. 7b shows in plan an alternative arrangement where the sensitive layers are omitted, and the two valves 701 and 702 are arranged in their open state to combine two input gas flows 703a and 703b in a single output gas flow 704.

Figure 7:
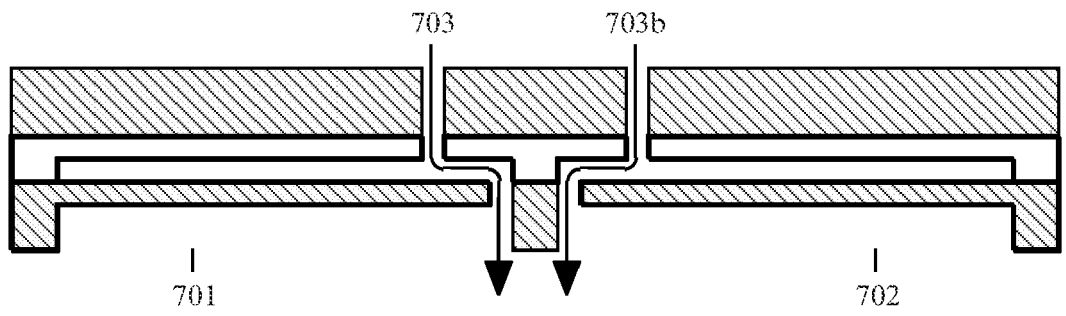
FIG. 7a shows a section view of two valves combined in a single substrate and FIG. 7b shows a plan view of the device layer, according to the present invention.
Figure 7:
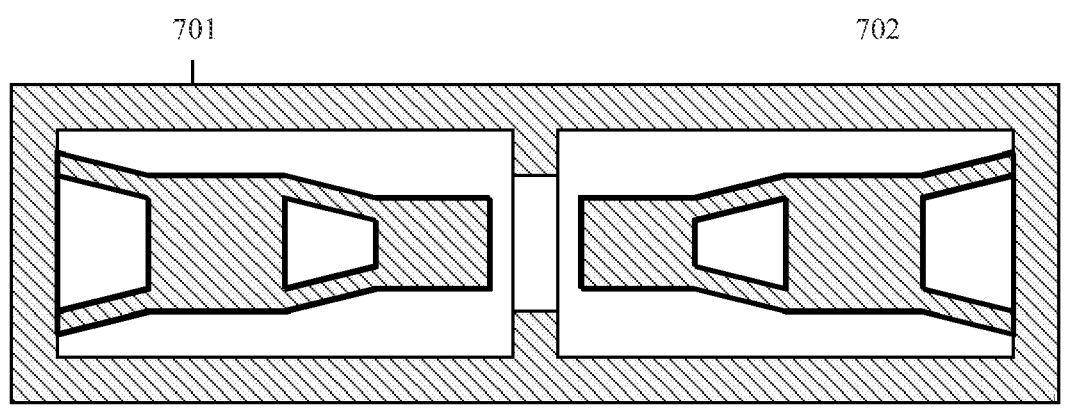

It will be apparent to those skilled in the art that elements of the type shown in FIGS. 6 and 7 may be stacked together. For example, FIGS. 8a and 8b both show in section an arrangement where a pair of valves 801 carrying chemically sensitive layers 810 constituting traps are stacked on top of a further pair of valves 802. The assembly is further stacked on top of a plate 803 comprising the input to a subsequent analysis system, and insulating layers 804 and 804b are provided therebetween.

This assembly can provide the action of a pre-concentrator previously described. For example, in FIG. 8a, the lower valves 802 are closed, and the upper valves 801 are opened. A gas stream may then flow from the input 805 to the output 806, passing over the chemically sensitive layers 810 and adsorbing thereon. In FIG. 8b, the upper valves 801 are closed and the lower valves 802 are opened. The upper valves 801 are heated, desorbing the adsorbed species, and the resulting gas stream 807 may pass out to the analysis system. The dead volumes in the arrangement shown are extremely small, since they comprise a set of small voids in an essentially planar structure.

Figure 8:
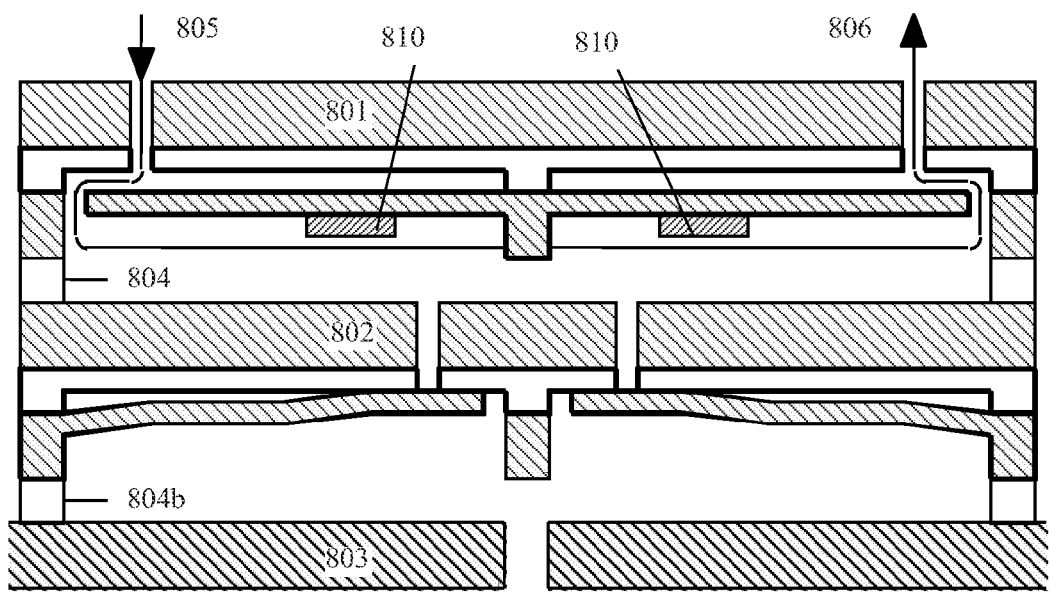
FIG. 8a shows a section view of a stacked assembly of devices and valves providing the adsorption step of chemical preconcentration.
FIG. 8b shows a section view of similar assembly providing the desorption step, according to the present invention.
Figure 8:
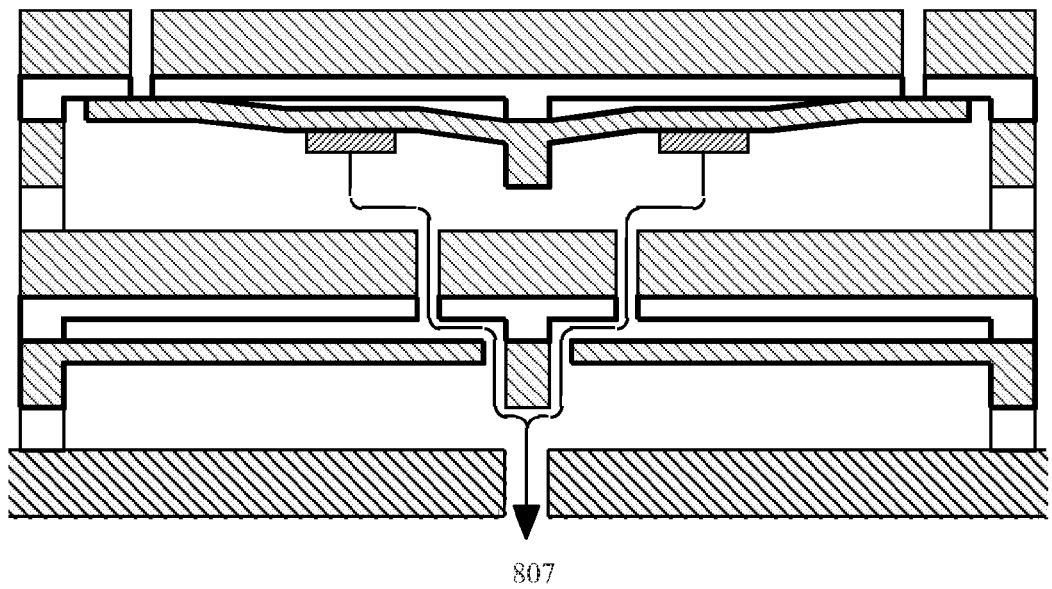

It will be appreciated that the preconcentrator system as shown in FIG. 8 may be provided in the form of a removable component, that may be attached externally to the analysis system. It will also be appreciated that different preconcentrators may be provided with different adsorbing layers, to suit different expected VOCs. Preconcentrators may also be provided in an array of similar devices, to increase the volume of concentrated gas, or in an array of differently sensitized devices.

It will be understood that the invention has been described with reference to preferred exemplary embodiments which for ease of explanation have been described with reference to specific figures. It will be fully appreciated that the arrangement of any one figure is not to be construed as limiting as the components or integers of a first figure or embodiment may be freely interchanged for those of another within the context of the claimed invention. Furthermore, the phrases "upper", "lower" and the like are provided for an understanding of the invention and are relative terms only as the invention may be deployed in configurations where one relative term may be interchanged for another.

Furthermore, it will be understood that the words comprises/comprising when used in this specification are to specify the presence of stated features, integers, steps or components but does not preclude the presence or addition of one or more other features, integers, steps, components or groups thereof.

The invention is not intended to be limited in any way except as may be deemed necessary in the light of the appended claims.

What is claimed is:

1. A pre-concentrator device configured to provide for a detection of one or more species present in a gas flow, the device including a trap through which the gas may flow, entry of gas into the trap through an orifice being controlled by a moveable membrane which is moveable between a first position wherein the gas is free to move through the orifice and into the trap and a second position wherein the membrane seals the orifice preventing the flow of gas into the trap, and wherein the membrane is provided with a chemically selective coating configured to selectively adsorb the species present in the gas during the flow of gas through the trap and wherein on sealing of the orifice the membrane is heatable so as to effect a desorption of the previously adsorbed species from the chemically selective coating.

2. The device as claimed in claim 1 wherein the moveable membrane is electrostatically operable.

3. The device as claimed in claim 1 wherein the orifice is provided through an insulating layer, a closure of the membrane effecting a contact between a portion of the membrane and the insulating layer.

4. The device as claimed in claim 3 wherein the membrane is moveable on application of a voltage between the membrane and a insulating substrate.

5. The device as claimed in claim 4 wherein a heating of the membrane is effected through application of an alternating voltage between the membrane and the substrate.

6. The device as claimed in claim 1 wherein the moveable membrane comprises a moveable flap suspended over the orifice by an elastic element.

7. The device as claimed in claim 3 wherein a insulating substrate comprises a semiconductor.

8. The device as claimed in claim 6 in which the chemically selective coating is provided in a mount and wherein each of the flap, the elastic element and the mount comprise a semiconductor.

9. The device as claimed in claim 6 in which the chemically selective coating is provided in a mount and wherein each of the flap, the elastic element and the mount comprise a metal.

10. The device as claimed in claim 7 in which the insulating substrate is an oxide of a semiconductor.

11. The device as claimed in claim 1 further including a valve, the valve configured to seal the trap on movement of the membrane to the second position.

12. A pre-concentrator system comprising:
at least one pre-concentrator device as claimed in claim 1, the trap defining an enclosure, the membrane providing a first valve and the enclosure including at least two further valves through which gas flow through the trap may be controlled.

13. The device as claimed in claim 1 wherein the chemically selective coating is integrally formed on a surface of the moveable membrane.

14. A device comprising an electrostatically operated valve and an electrically heated desorber, the electrostatically operated valve comprising:
a) a movable membrane comprising an elastic element on which a chemically selective coating is suspended above an orifice in an insulating layer wherein chemical molecules are operably adsorbed on the chemically selective coating from a gas stream flowing through the orifice,
b) the membrane is configured such that on application of a voltage between a substrate and the membrane, the membrane is deflected towards the substrate to block gas flow through the orifice, and,
c) the coating is resistively heatable to desorb the adsorbed chemical molecules by application of an alternating voltage between the substrate and the membrane, wherein, the chemically selective coating is provided on a desorber mount, each of the membrane, the elastic element and the desorber mount comprises a semiconductor, and the substrate comprises a semiconductor.

15. A device comprising an electrostatically operated valve and an electrically heated desorber, the electrostatically operated valve comprising:
a) a movable membrane comprising an elastic element on which a chemically selective coating is suspended above an orifice in an insulating layer; wherein chemical molecules are operably adsorbed on the chemically selective coating from a gas stream flowing through the orifice,
b) the membrane is configured such that on application of a voltage between a substrate and the membrane, the membrane is deflected towards the substrate to block gas flow through the orifice, and
c) the coating is resistively heatable to desorb the adsorbed chemical molecules by application of an alternating voltage between the substrate and the membrane, wherein the chemically selective coating is provided on a desorber mount, each of the membrane, the elastic element and the desorber mount comprises a metal, and the substrate comprises a semiconductor.

* * * * *